United States Patent [19]

Emerson et al.

[11] Patent Number: 5,738,861
[45] Date of Patent: Apr. 14, 1998

[54] METHOD AND COMPOSITION FOR DISINFECTION OF A CONTAMINATED ENVIRONMENT

[75] Inventors: Ralph W. Emerson; Bradford G. Crandall, Jr., both of Davis, Calif.

[73] Assignee: Proguard, Inc., Suisun City, Calif.

[21] Appl. No.: 561,706

[22] Filed: Nov. 22, 1995

Related U.S. Application Data

[62] Division of Ser. No. 485,002, Jun. 7, 1995.

[51] Int. Cl.$^6$ .................................................. A01N 25/34
[52] U.S. Cl. .................. 424/403; 424/405; 424/DIG. 10; 424/DIG. 11; 514/701
[58] Field of Search ........................ 424/403, 405, 424/DIG. 10, DIG. 11; 514/701

[56] References Cited

U.S. PATENT DOCUMENTS

| | | | |
|---|---|---|---|
| 2,465,854 | 3/1949 | Dorman | 167/30 |
| 4,097,607 | 6/1978 | Laroon | 424/324 |
| 4,402,950 | 9/1983 | Wolf et al. | 424/195 |
| 4,477,361 | 10/1984 | Sperti et al. | 252/106 |
| 4,978,686 | 12/1990 | Sotome | 514/698 |
| 5,149,715 | 9/1992 | Armstrong et al. | 514/701 |
| 5,166,317 | 11/1992 | Wallace et al. | 530/350 |
| 5,202,247 | 4/1993 | Kilburn et al. | 435/195 |
| 5,340,731 | 8/1994 | Kilburn et al. | 435/179 |
| 5,364,626 | 11/1994 | Masegawa | 424/403 |
| 5,486,537 | 1/1996 | Farinas | 514/462 |
| 5,536,501 | 7/1996 | Emerson et al. | 424/405 |

FOREIGN PATENT DOCUMENTS

| | | |
|---|---|---|
| 58-004702 | 1/1983 | Japan . |
| 58-201703 | 11/1983 | Japan . |
| 60-146804 | 2/1985 | Japan . |
| 61-228412 | 10/1986 | Japan . |
| 1261303 | 10/1989 | Japan . |
| 03268901 | 11/1991 | Japan . |
| 4149103 | 5/1992 | Japan . |
| 4176460 | 6/1992 | Japan . |
| 5117125 | 5/1993 | Japan . |
| 472623 | 12/1935 | United Kingdom . |
| 1023702 | 3/1966 | United Kingdom . |
| 1060447 | 3/1967 | United Kingdom . |
| 94/24158 | 10/1994 | WIPO . |

OTHER PUBLICATIONS

Chan et al, *AntiCancer Research* (1995) 15:703–708.
Herbert et al, *Fd Chem. Toxic* (1994) 32 No. 12, 1107–1115.
Mahmoud, A., *Letters In Applied Microbiology* (1994) 19:110–113.
Moleyar et al, *International Journal of Food Microbiology* (1992) 16:337–342.
Neudecker, Tilman, *Mutation Research* (1992) 227:173–185.
Yuan, et al, *Fd Chem. Toxic* (1992) 30 No. 12, 997–1004.
Casey & Dobb, *Enzymol. Microbiol. Technol.* (1992) 14:739–747.
Yuan et al., *Fund. & Applied Toxicol.* (1993) 20:83–87.
Bowles et al. 5. Food Protection 56:788–794.

*Primary Examiner*—Neil S. Levy
*Attorney, Agent, or Firm*—Viola T. Kung; Barbara Rae-Venter; Rae-Venter Law Group, P.C.

[57] ABSTRACT

The present invention provides methods and compositions for inhibiting microbial growth through the use of flavonoid aldehydes or alcohols for the purpose of disinfecting contaminated environments. The methods include the step of contacting the unsterile area with an amount of a flavonoid aldehyde or alcohol sufficient to control growth of pathogenic microbes. The aldehyde or alcohol can be provided in a variety of formulations.

3 Claims, No Drawings

METHOD AND COMPOSITION FOR DISINFECTION OF A CONTAMINATED ENVIRONMENT

CROSS-REFERENCE TO RELATED APPLICATIONS

This application is a divisional of U.S. application Ser. No. 08/485,002 filed Jun. 7, 1995 now pending.

TECHNICAL FIELD

The present invention involves disinfection of solid, liquid, and gaseous environments using flavonoid aldehydes and alcohols. The invention is exemplified by compositions comprising cinnamic aldehyde and coniferyl aldehyde to decontaminate areas colonized with microorganisms or areas subject to such colonization.

BACKGROUND OF THE INVENTION

Most terrestrial environments are colonized by microbes, some of which are potentially infectious pathogens. For example, solid surfaces including walls, floors, food preparation surfaces, and medical instruments often become contaminated by fungal, bacterial, or vital microorganisms. Similarly, such microorganisms often colonize liquids such as swimming pools, drinking water, and water used in food processing. Many microorganisms are airborne, traveling from one location to another and possibly spreading disease.

Currently available methods to control or eliminate microbial contamination suffer from several drawbacks. For example, antimicrobial agents are generally effective against only one microbial type. Antibacterial agents are generally ineffective against fungal organisms, and vice versa. Also, antimicrobial agents are often toxic to humans and other animals. Thus, it is of interest to develop compositions and methods that are useful for decontaminating a wide variety of environments.

RELEVANT LITERATURE

Wolf et al., U.S. Pat. No. 4,402,950 states that cinnamic aldehyde and certain other terpenes obtainable from aromatic plants are useful for deactivating viruses inside living human and animal organisms; Sperti et al., U.S. Pat. No. 4,477,361, describe the use of cinnamon compounds in soaps.

SUMMARY OF THE INVENTION

The present invention provides methods and compositions for inhibiting microbial growth through the use of flavonoid aldehydes or alcohols for the purpose of disinfecting contaminated environments. The methods include the step of contacting the unsterile area with an amount of a flavanoid aldehyde or alcohol sufficient to control growth of pathogenic microbes. The aldehyde or alcohol can be provided in a variety of formulations.

The biocidal product active ingredient used in the claimed methods and compositions has a structure shown in (1) below:

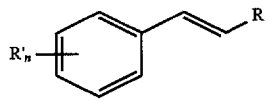

(1)

wherein R represents —CH$_2$OH or —CHO; n is an integer from 0 to 3; and each R$^1$ independently represents OH or an organic substitutent containing from 1 to 10 carbon atoms and from 0 to 5 heteroatoms, wherein the total number of carbon and heteroatoms in all R$^1$ substituents of said compound is no more than 15. These compounds include naturally occurring compounds such as cinnamaldehyde, coniferyl aldehyde and closely related compounds.

The invention finds use in controlling microbes in many environments where disinfection is desirable. The compositions and methods produce environments that are substantially free of microorganisms. Solid surfaces that have been decontaminated using the claimed composition and methods are another aspect of the invention, as are solid surfaces coated with a residue obtained by evaporation of a liquid composition that contains an effective microbial-growth-inhibiting amount of one or more of the flavonoid aldehydes or alcohols.

DETAILED DESCRIPTION OF THE PREFERRED EMBODIMENTS

The present invention provides methods which include at least one flavonoid aldehyde or alcohol in a formulation suitable for decontaminating an environment and/or producing an environment that is substantially free of microorganisms, and methods of using the compositions. The claimed methods involve contacting an environment with an effective amount of the compositions. As used herein, "decontaminate" means to disinfect or sterilize an environment that is colonized by microorganisms, or inhibit the growth of microorganisms in the environment. Such decontamination can occur immediately upon application of the biocidal agent, or can be a residual effect of preventing environments that are susceptible to microbial contamination from becoming contaminated. The environment can be liquid, gas or solid.

Compounds according to formula (1), unlike most other antimicrobials, are effective against both bacterial and fungal microbes, and are also effective against viruses. Another advantage of compounds of formula (1) is that they are nontoxic to humans and animals; a number of the aromatic and aliphatic aldehydes which may find use in the subject invention, such as benzaldehyde, acetaldehyde, cinnamaldehyde, piperonal, and vanillin are generally regarded as safe (GRAS) synthetic flavoring agents (21 CFR §172.515). The claimed compositions can be used in and/or around food sources. Additionally, the compositions can be used to impregnate organic matter which serves as a nutrient source for a target microorganism and/or can be provided bound to a solid support which itself is non-toxic to animals, including humans.

The claimed methods and compositions are useful for killing or inhibiting the growth of a wide variety of microorganisms. Examples of such organisms include fungi, bacteria (e.g., Salmonella, C. botulinum, M. tuberculosis, etc.), protozoa (e.g., Giardia), viruses, and algae. Of particular importance are organisms that are pathogenic to humans or other animals. Conveniently, the claimed methods and compositions are useful for decontaminating environments that are contaminated or susceptible to contamination with a single microbial species, or with multiple species.

The biocidal ingredients used in the claimed compositions and methods are flavonoid aldehydes or alcohols. The subject compound is as shown in formula (1) above. A preferred compound is shown in formula (2) below.

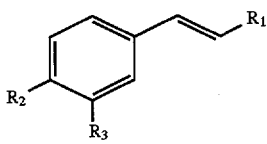

Wherein R represents —CHO, $R_2$ represents —H, —OH or an organic substituent containing from 1 to 10 carbon atoms, and $R_3$—H represents a methoxy group or organic substituent containing from 1 to 10 carbon atoms. Of particular interest are flavonoid aldehydes, particularly aromatic aldehydes. Examples of aromatic aldehydes that are of use in the present invention are cinnamic aldehyde ((3) below).

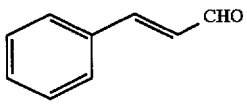

and coniferyl aldehyde ((4) below).

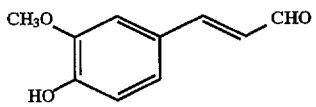

In addition to the specific compounds of the formulas (1), (2), (3) and (4) set forth above, derivatives of any of these compounds that produce a compound of the formula identified above upon action of a biological system on the derivative are considered to be equivalent to compounds of the invention. Thus application of precursor compounds to microorganisms that can metabolize the precursors to produce a specific compound identified above would be equivalent to the practice of the present invention. Biological conversion of precursor compounds into flavonoid aldehydes is described in, for example, U.S. Pat. No. 5,149,715 and references cited therein. See also Casey and Dobb, *Enzyme Microb. Technol.* (1992) 14: 739–747.

The claimed compositions typically consist of biocidal agents that are used alone or are contained in formulations that facilitate application of the biocidal agents to the environment to be decontaminated. The biocidal compounds are typically in the form of concentrated liquids, solutions, suspensions, powders and the like, containing such concentration of the biocidally active compound as is suited for a particular purpose at hand. For example, the compounds can be applied directly to an environment area susceptible to colonization by microbial organisms in the form of dilute solution in a suitable solvent. In one embodiment, the biocidal agents are formulated as aqueous emulsions. These aqueous compositions optionally contain a salt of a polyprotic acid such as sodium bicarbonate, sodium sulfate, sodium phosphate or sodium biphosphate. An emulsifier (Tween-80) also can be included in the formulation.

The biocidal ingredient is typically present in the formulations in an effective microbial growth-inhibiting amount. An "effective microbial growth-inhibiting amount" is that amount of biocidal ingredient that is effective in inhibiting the growth of microorganisms that are present in the environment or in preventing microorganisms from becoming established in the environment. Growth of a population of microorganisms is said to be "inhibited" if the microorganisms in the particular environment multiply at a lower rate in the presence of the biocidal agent than in an equivalent environment that is not treated with the biocidal agent. Preferably, the biocidal agent will result in the microorganisms multiplying at a rate that is less than about 70% of that observed for microorganisms in an untreated environment. More preferably, the rate of multiplication for microorganisms in a treated environment will be less than about 50%, and most preferably less than about 30% of that observed for microorganisms in an untreated environment.

An effective microbial growth-inhibiting amount of the flavonoid aldehyde or alcohol, when formulated as described herein, will typically be between 0.01 and 5.0 weight percent. More preferably, the concentration of the biocidal agent will be between 0.1 and 2.5 weight percent.

The biocidal aldehyde or alcohol compounds can be used either alone or in combination with other active or inactive substances. For use as a means of cleansing a surface, although the biocidal compound can be formulated alone as an aqueous solution, it also can be prepared as a soap or a detergent. Suitable detergents include anionic detergents such as those described in U.S. Pat. No. 4,978,686. The resulting emulsion is diluted to an appropriate concentration for use, and is additionally provided as a formulation suitable for the intended application, for example, as a household cleaner, carpet shampoo, detergent, or animal dip shampoo or soap. Generally, it is unnecessary to include antioxidants such as vitamin E, eugenol, BHT, n-propyl gallate and the like, in the formulation.

For some applications, the compounds can be bound to a solid support, either prior to or upon application to the environment that is to be decontaminated. For example, the biocidal compounds can be coupled to a solid support for application in powder or granular form, such as you use as pet litter or bound to paper or other material suitable for lining drawers or cupboards susceptible to contamination, for example, from insect or rodent droppings, and the like. Typically, the biocidal aldehydes and alcohols are coupled to the solid support by means of a bifunctional linker that has a moiety that is reactive with the aldehyde or alcohol and another moiety, such as a binding domain, that is reactive with the solid support. One can couple the biocidal aldehyde or alcohol to the binding domains with or without a cleavable bond; using methods well known to those skilled in the art. Where a solid carrier is used, the coupling reaction should avoid materials that can lead to oxidation of the active aldehydes. Examples of solid delivery systems include starch-dextran and the like. See, e.g., Yuan et al., *Fundamental and Applied Toxicology* (1993) 20: 83–87, for examples of delivery systems.

Another embodiment of the invention provides compositions useful for directly impregnating a surface with the biocidal agent so that the agent is bound to the surface. For example, where the environment to be decontaminated is a surface that comprises a polysaccharide such as cellulose, particularly microcrystalline cellulose, one can use a polysaccharide binding domain as a linker. For a surface that comprises cellulose, such as paper or wood, a cellulase binding domain is used as a linker. The preparation of cellulose binding domains is described in U.S. Pat. Nos. 5,340,731; 5,202,247 and 5,166,317. As an example, the flavonoid aldehyde-cellulase binding domain composition can be used to impregnate wood that is subject to or already colonized by microbes.

The formulations utilized in the claimed compositions and methods are typically free of substantive agents such as free fatty acids or emollients. For example, the formulations will contain less than 5 % by weight free fatty acids such as coconut fatty acid, tallow fatty acid, stearic acid, and oleic acid, as well as fatty acid ester soaps that contain free fatty acids or emollients such as glyceryl monostearate, hexadecyl stearate, diethyleneglycol dioleate, and the like. The formulations will also contain less than 5% weight percent of the emollients isopropyl myristate, isopropyl palmitate, isopropyl stearate, hexadecyl stearate, dihexadecyl adipate, and butyl stearate.

METHODS FOR DECONTAMINATING AN ENVIRONMENT

The invention also provides methods useful for decontaminating an environment that is colonized with microorganisms, or is subject to such colonization. These methods involve contacting the environment with an effective microbial-growth-inhibiting amount of one or more of the compounds shown in (2) above. The particular method used to "contact" an environment with the biocidal composition is not critical, as many methods are known.

The methods of the present invention are carded out by introducing into a target environment a sufficient amount of a biocidal agent to impair growth and/or viability of a microorganism and thereby decrease the population of that microorganism in the environment. A formulation containing the biocidal agent is introduced into the environment. For example, the formulation is sprayed on as a wet or dry formulation onto a material colonized by microorganisms, or a material susceptible to infestation with microorganisms. In some instances, time-release formulations may find use, particularly for applications to animals, or areas which are subject to recontamination, such as animal quarters.

Environments for which the claimed compositions and methods are useful include solids, gases, and liquids that are contaminated with microorganisms, or are susceptible to becoming contaminated. Foods and living humans or other animals are generally not considered environments for which the claimed invention is used. The environment may be contaminated with a single species of microorganism, or with multiple species.

1. Solids. The claimed invention is useful for decontaminating both porous and nonporous solids. Examples of nonporous solids include surfaces such as those used for food preparation. For example, surfaces used in butchering chickens, cattle, and other animals often become contaminated with microorganisms and are in need of decontamination, as are the carcasses of the butchered animals. Other solid surfaces for which the invention is useful include medical, dental, and surgical facilities, including the walls, ceilings and floors of the facilities, and medical instruments. Household surfaces such as ties and floors are also susceptible to contamination that one can prevent or remove by using the claimed methods and compositions. The invention also finds use in public sanitary facilities.

To decontaminate a nonporous solid environment, one can use any known method of contacting the solid with the biocidal composition. Such methods include spraying the biocidal composition on the solid, immersing the solid in the biocidal composition, and washing the solid with the composition.

Porous solids are also amenable to decontamination using the claimed methods and compositions. For a porous solid environment, in addition to those contacting methods described above for contacting a nonporous solid, one can filter or pass the biocidal composition through the porous solid or impregnate the solid with the composition. Porous solids for which the invention finds use include, for example, wound dressings and surgical gowns and face masks. By impregnating these porous solids with the biocidal agent, one can filter out air-borne contaminants (e.g.,
*Mycobacterium tuberculosis*, etc.) by passing the air through the impregnated porous solid, thus preventing the spread of infectious organisms. The impregnated porous solids are also useful for filtering liquids. In one preferred embodiment, the porous solid to be impregnated contains cellulose and the biocidal aldehyde or alcohol is linked to a cellulase binding domain, thus providing a means for attaching the biocidal agent to the solid.

2. Liquids. The claimed methods and compositions are also useful for decontaminating liquid environments. One example of a liquid environment for which the invention finds use is water, including drinking water, swimming pool water, stored water, humidifiers, waste water, medical waste, and food processing waste. The claimed compositions and methods are useful for decontaminating water applied to foodstuffs (e.g., chickens) during processing, including both the water that is to be used for cleaning the foodstuffs (upstream) as well as the waste water from the cleaning process (downstream). Biological fluids are another example of a liquid environment for which the claimed methods and compositions are useful.

To decontaminate a liquid using the claimed compositions, one can mix the claimed biocidal compositions with the liquid to be decontaminated. Alternatively, one can bind the biocidal agent to a porous solid support and pass the liquid through the support, as described above.

3. Gases. Gases, including air, are another environment that one can decontaminate using the claimed compositions and methods. For example, the invention is useful for decontamination or maintaining sterility of air in a room, such as an operating room or other medical treatment facility. One can use the invention to prevent airborne microorganisms from contacting a wound or other surface that is preferably kept free of contamination, and to prevent airborne microorganisms from being carried from one location to another. For example, one can use the invention to contain a pathogen such as *M. tuberculosis* within a particular room such as a tuberculosis ward, or to prevent a pathogenic microorganism from being spread on the exhaled breath of a person ill with an infectious disease that is caused by an airborne pathogen.

For decontaminating a gas, it is often desirable to bind the biocidal agent to a porous solid support. The gas is then decontaminated by passing it through the solid support. The binding of the biocidal agent to the support can be either covalent or noncovalent. The support used for this purpose can be any porous solid (e.g., cellulose). Specific applications of this embodiment include impregnation of room air filters, surgical masks and clothing, and wound dressings. Airborne contaminants are filtered from the air when the air passes through these porous supports that are impregnated with the biocidal agent. The method used to contact the support with the biocidal agent is not critical; a preferred method is filtering the biocidal agent composition through the porous support.

The invention also includes solid surfaces that have been decontaminated according to the methods described above. Such surfaces include solid surfaces that are coated with a residue obtained by evaporation of a liquid composition comprising an effective microbial growth-inhibiting amount of the biocidal agents described herein. The effective microbial growth inhibiting amount comprises 0.1 to 5.0 percent by weight of the residue. Preferably, the residue will have a non-greasy texture.

The following examples are offered by way of illustration and not by way of limitation.

EXAMPLES

All experiments run with test formulations include a positive active ingredient control and a negative formulation-without-active-ingredient control over a concentration range of at least two log units to give sufficient data to calculate an IC50.

Example 1

The components of a formulation to be used for a particular application can be determined by constructing a dose response curve by evaluating first the concentration range over which a given component has no activity to where it provides maximum activity and then evaluating this component separately and in combination with the components of interest for a given formulation. As an example, the effects of cinnamic aldehyde in a range from 0.01 and 5.0 weight percent against *B. subtilus, B. megaterium, C. botulinum* and Salmonella is evaluated. An IC50 , the inhibitory concentration at which 50% control of each organism for each formulation tested is obtained. The efficacy of the formulation can be increased by using higher doses of cinnamic aldehyde, and/or adding other compounds of formula (1), or by increasing the substantiveness of the formulation by adding detergent, and the like. The antipathogenic effect of a particular formulation on a given pathogen is then measured for each formula and component with or without a serial dilutent of any additional component of interest. Optimal dose-ranges are calculated in vitro and in vivo using techniques known to those of ordinary skill in the art. Preferred formulations provide a substantially decontaminated environment.

Surface Sterilization Bioassay

Using a surface that would simulate a hospital surface (tile) or a medical instrument, or a food-preparation surface test varying concentrations of the formulations of interest for positive control of the growth of microorganisms.

Waste Water Treatment

Using the food-processing waste water, for example, from a chicken-processing plant, survey for a typical microbial population. Then, demonstrate concentration at which the growth of a selected bacteria (for example, Salmonella) is inhibited.

Disinfection of Air

Impregnate permeable cotton cloth with varying concentrations of the test formulation, place the cloth in a glass jar, and survey the area surrounding a jar inoculated with bacteria or viruses for spread of the contamination over a defined period of time.

Example 2

Activity of cinnamic aldehyde and/or coniferyl aldehyde against mold and mildew is determined in a similar fashion to that described in Example 1.

Example 3

Activity of cinnamic aldehyde and/or coniferyl aldehyde against influenza A virus is determined in a similar fashion to that described in Example 1.

Example 4

Activity of cinnamic aldehyde and/or coniferyl aldehyde against protozoa or algae is determined in a similar fashion to that described in Example 1. For example, the minimum inhibitory concentration (MIC) and dose response for Giardia and swimming pool algae are determined.

Stored Water Biossay

Using chlorine as a positive control, run a large volume (4 1) experiment out of doors. Determine the concentration of the test formulation varying concentrations of cinnamic aldehyde that is needed to inhibit organism growth for a measured length of time (time to retreatment).

Unless defined otherwise, all technical and scientific terms used herein have the same meaning as commonly understood by one of ordinary skill in the art to which this invention belongs. All publications and patent documents referenced in this application are incorporated herein by reference to the same extent as if each individual publication or patent application was specifically and individually indicated to be incorporated by reference.

It is understood that the examples and embodiments described herein are for illustrative purposes only and that various modifications or changes in light thereof will be suggested to persons skilled in the art and are to be included within the spirit and purview of this application and scope of the appended claims.

What is claimed is:

1. A composition comprising:

a porous solid selected from the group consisting of a wound dressing, a surgical gown, and a face mask impregnated with 0.01 to 5.0% by weight of a biocidal compound comprising one or more compounds selected from the group consisting of cinnamic aldehyde and coniferyl aldehyde by filtering an aqueous composition comprising said biocidal compound through said porous solid.

2. A composition comprising:

a porous solid which comprises a room air filler or a filter for a liquid environment impregnated with 0.01 to 5.0% by weight of a biocidal compound comprising one or more compounds selected from the group consisting of cinnamic aldehyde and coniferyl aldehyde by filtering an aqueous composition comprising said biocidal compound through said porous solid.

3. The composition according to claim 1 or claim 2, wherein said amount is sufficient to limit multiplication of microorganisms contacting said porous solid to a rate less than about 70% of that observed for microorganisms contacting an untreated porous solid.

* * * * *